United States Patent [19]

Sawai et al.

[11] Patent Number: 5,279,835
[45] Date of Patent: Jan. 18, 1994

[54] BINDER-FREE ORALLY ADMINISTRABLE TABLET CONTAINING 3-OXYGERMYLPROPIONIC ACID

[75] Inventors: Kiichi Sawai; Masayasu Kurono; Takahiko Mitani; Yasuaki Kondo; Makoto Sato; Yoshiro Ishiwata; Syoji Yokochi; Toshiyuki Kouzaki, all of Nagoya, Japan

[73] Assignee: Sanwa Kagaku Kenkyusho Co. Ltd., Nagoya, Japan

[21] Appl. No.: 906,465

[22] Filed: Jun. 30, 1992

[30] Foreign Application Priority Data

Jul. 1, 1991 [JP] Japan .................. 3-159343

[51] Int. Cl.$^5$ ................. A61K 9/20
[52] U.S. Cl. ................. 424/465; 424/464; 514/492
[58] Field of Search ........... 424/465, 464; 514/184, 514/492

[56] References Cited

U.S. PATENT DOCUMENTS 4,889,715  12/1989  Sawai et al. ............ 424/78.05
5,008,416  4/1991   Kurono et al. ............ 424/650

FOREIGN PATENT DOCUMENTS 186505  7/1986  European Pat. Off. .
435693  7/1991  European Pat. Off. .

*Primary Examiner*—Thurman K. Page
*Assistant Examiner*—James M. Spear
*Attorney, Agent, or Firm*—Armstrong, Westerman, Hattori, McLeland & Naughton

[57] ABSTRACT

A 3-oxygermylpropionic acid preparation is provided, which activates the action of 3-oxygermylpropionic acid having the general formula:

$[(O_{\frac{1}{2}})_3GeCH_2CH_2COOH]_n$ wherein n = an integer of at least 1 and is readily solubilized and disintegrated in vivo. The present preparation is manufactured by compression-molding at high pressure a composition comprising 3-oxygermylpropionic acid and two or more low-molecular substance of high solubility in water. The low-molecular substances are selected from the group consisting of white sugar, sorbitol, fructose, sucrose, glucose, lactose, mannitol and sodium chloride.

1 Claim, No Drawings

BINDER-FREE ORALLY ADMINISTRABLE TABLET CONTAINING 3-OXYGERMYLPROPIONIC ACID

BACKGROUND OF THE INVENTION

1. Field of the Invention

The present invention relates generally to a composition containing 3-oxygermylpropionic acid (hereinafter 3-OGP for short) having the following general formula:

$[(O_{\frac{1}{2}})_3GeCH_2CH_2COOH]n$ wherein n=an integer of at least 1 and, more particularly, to a pharmaceutical solid preparation comprising 3-OGP and a low-molecular substance of high solubility in water, which is well solubilized and disintegrated in vivo so that the pharmacological activity of 3-OGP can be much more improved than ever before.

2. Statement of the Prior Art

The pharmacological activity of 3-OGP, because it has complex polymerizability and a variety of applications, has recently attracted attention, and the antiviral activity of this compound has been known for long as well. In this regard, see JP-P-57-53800, etc.

We have made intensive studies not only of compositions for enabling 3-OGP to maintain its own pharmacological activity stably but of how it acts in vivo as well. We have thus already found that a variety of substances can be effectively used as stabilizers for 3-OGP (see JP-A-61-65819) and that some lactoses can enhance its activity (see JP-A-60-190714).

We have also discovered that some amine salts of 3-OGP are effective (JP-A-1-139587).

Organogermanium compounds have been known for long to have a variety of pharmacological activities not found in other compound systems. However, they are not commercially used as pharmaceutics as yet, because of their disadvantages of differing in action from lot to lot and being unclarified in terms of some specific activities (see JP-P-46-2964 and 58-44677).

In general, when propionic acid drugs are administrated to patients in solid preparation forms, they stimulate the mucosas of the gastrointestinal tracts and are relatively slowly absorbed in the internal organs. In some cases, however, their absorption is delayed or inhibited. For this reason, various forms of drugs such as effervescent ones are now proposed.

However, 3-OGP has some pharmacological problems. For instance, because of its complex polymerizability, 3-OGP is so susceptible to changes in the degree of polymerization due to pressure, moisture, heat, light, etc. that its physico-chemical properties can be likely to vary elusively when manufactured by known drug-making procedures. In addition, the pharmacological activity of 3-OGP is independent on dose and may rather drop at high dose.

So far, we have made studies of how the activity of 3-OGP is stabilized by polymeric compounds, and have now found that when 3-OGP drugs are prepared (in the form of dry tablets) by high-pressure drug-making procedures that are easy to carry out, their activities may often drop, and this is primarily caused by the application of high pressure.

Incidentally, the cytopathogenicity, esp., organopathogenicity and teratogenicity of medicines, toxic substances and radiation appear as side effects in the case of medicines and as social problems such as environmental pollution in the case of toxic substances. However, nothing is done to solve these problems with the exception of some toxicides.

When administrated to those who suffer from organic dysfunctions, esp., patients with hepatitis and nephritis, medicines are likely to produce harmful side effects, causing the patients to suffer from disorders such as anaphylaxy and acute organic dysfunctions and, in the worst case, die.

Drugs having strong cytopathogenicity such as anti-cancer drugs containing cytotoxins and inhibitors for nucleic acid synthesis have generally strong toxicity to internal organs, and this is the reason why drugs are called a double-edged sword.

A sort of addicts like habitual drinkers and smokers and those who have taken in toxicic substances such as methyl mercury and heavy metal ions suffer from tissular cytopathogenicity and organic disorders, posing social problems. It is considered that all these problems can never be solved without eliminating the causes. Drugs having strong cytopathogenicity or high toxicity to internal organs have similar problems, but they may be eliminated, or at least reduced, by using such drugs in small doses or not using such drugs at all. In some cases, however, these drugs must be urgently administrated to patients with cancer, infectious diseases or other disorders or pregnant women. Thus, there is still a demand for developing how to use such drugs with great safety.

It is an object of this invention to provide a 3-OGP preparation in solid forms which can not only be used with great safety but without degeneration but can also be manufactured simply.

In this connection, it is noted that the 3-OGP used in the present invention is a white acicular crystal having such physicochemical properties as expressed by a specific gravity or density of 2.23, a solubility in water of 1.57 at 20° C. and a melting point of ca. 230° C.

SUMMARY OF THE INVENTION

According to this invention, the aforesaid object is achieved by the provision of a solid preparation which is manufactured by compression-molding a composition comprising 3-OGP and a low-molecular substance of high solubility in water at high pressure. This 3-OGP preparation maintains the activated action of 3-OGP, and is easily solubilized and disintegrated in vivo.

Preferably, the 3-OGP preparation of this invention is in a tablet form for oral administration which is obtained by compression-molding at high pressure a composition comprising 1 to 10% by weight of 3-OGP and 80% by weight or more of at least two low-molecular substances of high solubility in water, selected from the group consisting of white sugar, sorbitol, fructose, sucrose, glucose, lactose, mannitol and sodium chloride.

In a more preferable embodiment of this invention, the 3-OGP preparation is manufactured by compression-molding at high pressure a composition comprising 3-OGP and white sugar, sorbitol and fructose at a 20:5-7:1 ratio optionally together with small amounts of vehicles, binders and disintegrators in conventional manners.

It is found that the 3-OGP drug of this invention maintains 3-OGP without disintegration during drug-making and so is more stable during storage and more readily solubilized and disintegrated or more active in vivo than those obtained by compressing at high pressure compositions containing polymeric substances, esp., carboxymethylcellulose hydroxypropylmethylcellulose, hydroxypropylcellulose, polyvinyl pyrrolidone and Polyethylenglycol. Thus, when preparations are manufactured by high-pressure compression, the use of polymeric substances should be avoided as much as possible. This is also ture of even when smaller amounts of vehicles, binders and disintegrators are used.

The solid 3-OGP preparation of this invention is found to be efficacious for preventing and treating cytopathogenic disorders caused by cytopathogenic substances such as radiation like X- or γ-radiation or a radioactive substance, an ulcerogenic substance like indomethacin, a nurotoxin or nephrotoxin like carbon monoxide or kanamycin, a nucleic acid synthesis-inhibiting, teratogenic substance like 5-FU, and alcohol, carbon tetrachloride or a hepatotoxic organism like a hepatitis-inducing virus.

The solid preparations of this invention may be usually provided as compressed tablets for oral administration, and may be used in the form of troches, pills and suppositories as well.

It is understood that the dose of 3-OGP, when administrated to patients, depends on in what form it is used, the patients' age, etc., but generally lies in the range of 1 to 1500 mg/kg, if used in combination with antipyretics, antiphlogistics and lenitives. When orally administrated to adult patients (50 kg), 3-OGP should preferably be used at a dose of about 150 mg/day.

EXAMPLES

The effects of this invention will now be explained more specifically but not exclusively with reference to composition and pharmacological examples.

Example 1

Compressed Tablet

A compressed tablet was prepared according to the following recipe.

| | |
|---|---|
| 3-OGP | 10.0 |
| Lactose | 158.2 |
| CMC-Na | 8.0 |
| Light silicic anhydride | 2.0 |
| Magnesium stearate | 1.8 |
| | 180.0 mg |

Example 2

Compressed Tablet

A compressed tablet was prepared according to the following recipe.

| | |
|---|---|
| 3-OGP | 10.0 |
| Lactose | 103.2 |
| Corn starch | 40.0 |
| Cellulose Microcrystalline | 25.0 |
| Magnesium stearate | 1.8 |
| | 180.0 mg |

Example 3

Compressed Tablet

A compressed tablet was prepared according to the following recipe.

| | |
|---|---|
| 3-OGP | 10.0 |
| White sugar | 84.0 |
| Sorbitol | 84.0 |
| Magnesium stearate | 2.8 |
| | 180.0 mg |

Example 4

Compressed Tablet

A compressed tablet was prepared according to the following recipe.

| | |
|---|---|
| 3-OGP | 10.0 |
| Sodium chloride | 164.6 |
| Talc | 2.7 |
| Magnesium stearate | 2.7 |
| | 180.0 mg |

Example 5

Compressed Tablet

A compressed table was prepared according to the following recipe.

| | |
|---|---|
| 3-OGP | 10.0 |
| White sugar | 125.3 |
| Sorbitol | 41.7 |
| Fructose | 1.2 |
| PVP K-30 | 2.7 |
| Magnesium stearate | 1.8 |
| | 180.0 mg |

Example 6

Compressed Tablet

A compressed tablet was prepared according to the following recipe.

| | |
|---|---|
| 3-OGP | 10.0 |
| White sugar | 125.3 |
| Sorbitol | 41.7 |
| Fructose | 1.2 |
| HPC-L | 3.0 |
| Magnesium stearate | 1.8 |
| | 180.0 mg |

It is noted that all Examples 1–6 use compositions for activating 3-OGP.

Reference Example a

| | |
|---|---|
| 3-OGP | 10.0 |
| Lactose | 153.2 |
| CMC-Na | 8.0 |
| PVP K-30 | 8.0 |
| Magnesium stearate | 1.8 |
| | 180.0 mg |

Reference Example b

| | |
|---|---|
| 3-OGP | 10.0 |
| White sugar | 165.2 |
| HPC-L | 3.0 |
| Magnesium stearate | 1.8 |
| | 180.0 mg |

It is noted that both Reference Examples a and b use compositions containing polymeric substances.

Pharmacological Tests

1) Immune Response—Enhancement of Immune Control Action

The effects of 3-OGP, salts and hydroxypropylcellulose incorporated in compositions were investigated by delayed type hypersensitivity reactions (DTH reactions) using sheep red blood cells (SRBCs) as antigens.

1-A) Compositions used for testing

Used to this end were the preparations according to Example 1–5 and Reference Examples a and b.

1-B) Testing Procedures

Sarcoma-180 cells ($10^6$) were intraperitoneally transplanted in test animals—ICR mice (seven-week old), 10 for each group. Then, SRBCs ($10^6$) were injected into each animal through the vein of the tail for sensitization.

Four days later, SRBCs ($2 \times 10^8$) were injected into the pododerm of the right hind leg to induce the DTH reaction and, 24 hours later, the thickness of the pododerm was measured. Note that the test drugs were administered to the animals in the form of a feed mix 4 days before sensitization.

1-C) Results

The results are set out in Table 1, from which it is found that the compositions of this invention are closer to the normal value than 3-OGP, indicating that the activity of 3-OGP is much improved.

TABLE 1-1

Recipe Permutation of DTH activity
(1) Sugar Coating Recipe > (2) Binder-Free Recipe > (3) Conventional Recipe
(1) Sugar Coating Recipe: Recipe 12 > Recipe 11
(2) Binder-Free Recipe: Recipe 7 > Recipe 9 > Recipe 6 > Recipe 4
(3) Conventional Recipe: Recipe 3 > Recipe 1

Results of DTH Assay

|  | Dose in mg/kg | Pododerm Swelling ($\times$ 0.01 mm Average Stadard Deviation n = 10) |
|---|---|---|
| SMG |  | 115.4 11.2*** |
| MGWC |  | 47.1 3.8 |
| 3-OGP | 0.1 | 55.1 3.3 |
|  | 1 | 73.8 5.7** |
|  | 10 | 70.2 5.1** |
| R. Ex. a | 0.1 | 62.1 6.3 |
|  | 1 | 68.8 4.1** |
|  | 10 | 65.8 3.5** |
| R. Ex. b | 0.1 | 59.6 3.8 |
|  | 1 | 70.3 5.8** |
|  | 10 | 68.2 5.6** |
| SMG |  | 117.4 11.1*** |
| MGWC |  | 48.9 3.2 |
| 3-OGP | 0.1 | 64.3 6.4 |
|  | 1 | 72.1 5.5** |
|  | 10 | 66.3 3.1** |
| R. Ex. 1 | 0.1 | 68.8 5.8** |
|  | 1 | 85.0 5.9*** |
|  | 10 | 74.3 4.9*** |
| R. Ex. 2 | 0.1 | 69.3 5.4** |
|  | 1 | 84.8 3.9*** |
|  | 10 | 75.8 4.2*** |
| R. Ex. 3 | 0.1 | 68.9 4.8** |
|  | 1 | 89.3 6.3*** |
|  | 10 | 76.7 3.2*** |
| R. Ex. 4 | 0.1 | 69.2 5.2** |
|  | 1 | 87.4 5.0*** |
|  | 10 | 76.0 4.9*** |

SMG: Sound Mouse Groups
MGWC: Mouse Groups With Cancer
Significant difference with respect to the mouse groups with cancer
*p < 0.05, p < 0.01, *p < 0.001

TABLE 1-2

|  | Dose in mg/kg | Pododerm Swelling ($\times$ 0.01 mm Average Standard Deviation n = 10) |
|---|---|---|
| SMG |  | 115.5 10.4*** |
| MGWC |  | 55.5 5.8 |
| 3-OGP | 0.1 | 63.5 7.2 |
|  | 1 | 77.0 8.2** |
|  | 10 | 73.2 5.1* |
| R. Ex. 5 | 0.1 | 95.5 7.3*** |
|  | 1 | 105.0 9.2*** |
|  | 10 | 109.2 7.1** |
| R. Ex. 6 | 0.1 | 101.8 7.5*** |
|  | 1 | 113.3 8.9*** |
|  | 10 | 110.2 7.8** |

2) Inhibition of Renal Cytopathogenicity—Effect of 3-OGP Compositions on Preventing Nephritis 2-A) Purpose The effect of 3-OGP on preventing spontaneous nephritis in MRL/1 mice was investigated.

2-B) The preparation of Ex. 6 was orally administrated to test animals—MRL/1 mice of six-week old, 15 for each group—at daily doses of 0.1 mg/kg, 1.0 mg/kg and 10.0 mg/kg calculated as 3-OGP twice a week over 12 weeks. It is noted that this preparation was administrated to each animal in the form of a feed mix. Once a week, urinary protein was measured to find how many animals were positive or had a urinary protein concentration of 100 mg/dl or more. In addition, the urea nitrogen content of blood on the day following the final administration were measured to make sero-biochemical as well as histopathological estimations of the action of the 3-OGP compositions on nephritis.

It is noted that the urinary protein was determined with Protein Pretest (made by Wako Junyaku) and the urea nitrogen content of blood was estimated with Urea Nitrogen Test B: Urease/Indophenol Method (made by Wako Junyaku).

3-C) Results and Considerations

In the control group not treated with 3-OGP, a urinary protein increase was observed after 9 to 10 weeks. In the groups treated with 3-OGP, however, any urinary protein increase was not found. In the group treated with 10 mg/kg of 3-OGP in particular, the increase in urinary protein was significantly inhibited even after 12 weeks. In this regard, see Table 2.

This was true of the urea nitrogen content of blood; in the group treated with 10 mg/kg of 3-OGP, the increase in it was significantly inhibited. In this regard, see Table 3.

The nephritis induced in the MRL/1 mice was mainly membranous glomerulonephritis. In the control group, 60% of the glomeruli showed lesion severer than mediocre membranous glomerulonephritis, in contrast to only 20–36% in the group treated with 3-OGP. This suggests that the 3-OGP composition of this invention significantly inhibits nephritis spontaneously induced in the MRL/1 mice.

As will be understood from Tables 2 and 3 given below, the 3-OGP compositions are efficacious against nephritis induced in the MRL/1 mice from both the sero-biochemical and histopathological standpoints.

TABLE 2

| 3-OGP | Urinary Protein in % | | |
|---|---|---|---|
|  | After 10 weeks | After 11 weeks | After 12 weeks |
| Control | 52.3 | 66.6 | 91.3 |
| 0.1 mg/kg | 28.7 | 47.1 | 65.6 |
| 1 mg/kg | 28.1 | 23.8 | 51.0 |

TABLE 2-continued

| 3-OGP | Urinary Protein in % | | |
|---|---|---|---|
| | After 10 weeks | After 11 weeks | After 12 weeks |
| 10 mg/kg | 15.8 | 27.5 | 53.3 |

TABLE 3

| Urea Nitrogen Content of Blood | |
|---|---|
| 3-OGP | BUN in mg/kg |
| Control | 41 4.1 |
| 0.1 mg/kg | 33 1.3 |
| 1 mg/kg | 29 3.7 |
| 10 mg/kg | 30 0.2 |

3) Inhibition of Enchephalic Cytopathogenicity Effect of 3-OGP Compositions on Amnesia due to the Inhalation of Carbon Dioxide 3-A) Testing Procedures A ddy male mouse was placed in a bright chamber of a bright and dark box (comprising a bright chamber and a dark chamber, both being of 15.0×17.5×18.5 cm and including an inlet/outlet combination of 6.0×6.0 cm) to measure the length of time by the time when the mouse walked into the dark chamber (the reaction potential time during acquisition, hereinafter abbreviated as A.T.). From just after the animal walked into the dark chamber, foot shocks of 2.5 mA were continuously applied to the animal through a floor's grid with a shock generator scrambler, manufactured by Astech Co., Ltd., until the animal again walked into the bright chamber. Immediately after the acquisition trial, the animal was placed in a desiccator, and a $CO_2$ gas (15 l/min) was injected into the desiccator for 40 to 45 seconds till apnoea. After the animal was removed from the desiccator, artificial aspiration was immediately tried thereon. The animal was then put back to a home cage.

After 24 hours of the acquisition trial, the animal was again placed in the bright chamber of the bright/dark box to measure the length of time by the time when the animal walked into the dark chamber (the reaction potential time during the retention trial, hereinafter abbreviated as R.T.).

3-B) Results and Considerations

The results of the dysmnesia models induced by CO gas loading are set out in Table 4, from which it is understood that the 3-OGP composition increases the reaction potential time (R.T) during the retention trial significantly, suggesting an effect on the amelioration of dysmnesia.

TABLE 4

| Dysmnesia Model Test Results | | | |
|---|---|---|---|
| Group | Number of Animals | A.T. in sec. | R.T. in sec. |
| A | 30 | 47.4 8.4 | 266.4 33.5 |
| B | 15 | 50.4 35.6 | 360.0 00 |
| C | 15 | 56.5 2.8 | 70.0 10.0 |

Group A: Received orally a feed mix containing the pulverized preparation of Ex. 5 (10.0 mg/kg/day of 3-OGP) from the three days before the initiation of testing as well as foot shocks plus $CO_2$ gas.
Group B: Foot shocks without $CO_2$ gas.
Group C: $CO_2$ gas without foot shocks.

4) Inhibition of Hepatic Cytopathogenicity Induced by Hepatotoxin

4-A) Test drug

Used to this end were feed mixtures containing the pulverized preparation of Ex. 5 and 3-OGP.

4-B) Testing Procedures

A solution (5 ml/kg) of carbon tetrachloride (0.18% v/v, 14.4 mg/kg) was intraperitoneally administrated to an animal—Crj:CD-1 (ICR) mice of five-week old, 10 for each group—to induce hepatopathy. The test groups received the test substances once a day over five days, provided that before administration, they were fasted for 10 hours. After 30 minutes of the final drug administration, carbon tetrachloride was administrated to the animal. To what extent hepatopathy was induced was estimated by collecting an amount of serum by the method described in "Kiso To Rinsho", Vol. 24, No. 1, Jan. 1990, pp. 337-344 and determining AST (L-aspartate:2-oxogulutarate aminotransferase and ALT (L-alanine:2-oxogulutarate aminotransferase), indices to hepatocyte disorders and ALP (alkaline phosphatase) and LAP (leucine aminopeptidase), indices to cholangitis or other similar disoders.

The results are set out in Table 5, indicating that the administration of the drugs reduces the amount of enzymes released in association with hepatocyte disoders. So far, it has been known that the activity of 3-OGP may drop at high dose and vary irrespective of dose. According to this invention, however, it has turned out that if 3-OGP is incorporated in the composition of this invention, its activity is then stabilized depending on dose.

TABLE 5

| | Serum Enzyme Changes (IU/L) | | | |
|---|---|---|---|---|
| Control Group | AST | ALT | ALP | LAP |
| ($CCl_4$ alone) | 16500 20 | 10500 15 | 360 20 | 140 10 |
| Groups receiving drugs Dose | | | | |
| a) Preparation of Ex. 5 | | | | |
| 0.1 mg/kg | 8700 30 | 4800 20 | 260 30 | 100 10 |
| 1 mg/kg | 7100 30 | 4800 20 | 260 30 | 100 10 |
| 10 mg/kg | 6900 20 | 4700 20 | 240 20 | 90 10 |
| b) 3-OGP | | | | |
| 0.1 mg/kg | 10500 30 | 6100 20 | 300 30 | 100 10 |
| 1 mg/kg | 7000 20 | 4800 15 | 260 20 | 100 10 |
| 10 mg/kg | 12000 25 | 7600 20 | 360 20 | 130 10 |

5) Preventing of Radiation Disorder

5-A) Test Drug

Used to this end was the preparation of Ex. 6. 5-B) Testing Procedures

For test animals, ddy male mice of five-week old were used, 10 for each group. It is noted that an antibiotic was administrated to all the mice so as to prevent infection of the enterobacteria.

Using a soft X-radiation irradiator, the mice were exposed to soft X-radiation at an equal voltage of 140 kv and a dose of 650 roentgens to measure the survival rate and average survival days after 30 days.

The test drug in the form of a 0.5% gelatin solution was orally administrated to the animals once immediately after exposure, or it was orally and continuously administrated to the animals thrice over 3 days immediately after exposure. 5-C) Results The results are set out in Table 5, from which it is found that the groups receiving the 3-OGP composition of this invention are more significantly increased in terms of the survival rate and average survival days than the control group. This indicates that the 3-OPG composition of this invention is clearly efficacious against preventing radiation disorders.

TABLE 6

| Group | Survival Rate in % | Average Survival Days |
| --- | --- | --- |
| Control | 10 | 12.0 |
| 1 mg/kg once | 20 | 15.3 |
| 10 mg/kg once | 40 | 19.8* |
| 100 mg/kg once | 50 | 20.8* |
| 1 mg/kg thrice | 30 | 19.1* |
| 10 mg/kg thrice | 40 | 19.9* |
| 100 mg/kg thrice | 50 | 21.6* |

*there is a significant difference with respect to the control group at a significant level $p < 0.05$.

As mentioned above, the present invention provides a 3-OGP preparation which is obtained by high-pressure compression easy to carry out. This preparation is unlikely to undergo chemical changes in the presence of moisture, easily usable, readily disintegrated and absorbed in vivo, and maintains the pharmacological action of 3-OGP.

The solid 3-OGP preparation (tablet) of this invention may be used in combination with other drugs, and is effective as inhibitors for cytopathogenic disorders, esp., disorders of internal organs such as the liver and kidney by toxic substances and as drugs for preventing and treating radiation disorders.

The 3-OGP preparation of this invention can not only be used, with great safety, in combination with other drugs but can also be readily solubilized and disintegrated in vivo and produce its own activity depending on dose.

Thus, the 3-OGP preparation of this invention has a number of advantages. Among them:

It can be used as medicaments for preventing and treating organic disorders induced by drugs of strong toxicity and radiation, esp., hepatic disorders caused by toxic organisms such as hepatitis virus.

It can be used for patients with organic diseases, brain diseases and cell-related diseases, pregnant women or children with active proliferation of the cells, when they have cancer or infectious diseases, thereby reducing the side effects of drugs for treating such diseases and so using them with great safety.

It can be used for restoring cells lesioned by coming into contact with strongly cytopathogenic substances or substances having strong toxicity to internal organs.

It can be administered to workers likely to handle reagents and chemicals of strong toxicity, a sort of drug addicts such as habitual drinkers and smokers or chronical pathogenic virus carriers to prevent them from having organic diseases or becoming serious.

What we claim is:

1. An orally administrable tablet prepared by compression molding a mixture consisting of 1-10 wt % of 3-oxygermylpropionic acid and at least one water soluble material selected from the group consisting of sorbitol mannitol and sodium chloride.

* * * * *